United States Patent [19]

Dorffer et al.

[11] 4,057,069
[45] Nov. 8, 1977

[54] METHOD OF NERVE STIMULATION AND A STIMULATOR FOR THE APPLICATION OF THE METHOD

[75] Inventors: Auguste Dorffer, Grenoble; Jean-François Piquard, Vizille, both of France

[73] Assignee: Commissariat a l'Energie Atomique, Paris, France

[21] Appl. No.: 607,688

[22] Filed: Aug. 25, 1975

[30] Foreign Application Priority Data

Aug. 30, 1974  France .............................. 74.29645

[51] Int. Cl.² .......................................... A61N 1/36
[52] U.S. Cl. ................................................. 128/421
[58] Field of Search ...... 128/419 C, 419 EF, 419 PG, 128/419 R, 421, 422, 423

[56] References Cited

U.S. PATENT DOCUMENTS

3,662,758  5/1972  Glover ............................ 128/419 E
3,667,477  6/1972  Susset et al. ..................... 128/419 E
3,773,051  11/1973  Holcomb et al. .................. 128/422

*Primary Examiner*—William E. Kamm
*Attorney, Agent, or Firm*—William R. Woodward

[57] ABSTRACT

In order to excite living cells, a FM transmitter transmits for a period $t$ at a frequency $f$ such that the difference between $f$ and a reference frequency $f_O$ sets the amplitude of a desired nerve stimulation pulse. A receiver implanted in the living body is inductively coupled to the transmitter and processes the signal so as to obtain an output signal having an amplitude which is proportional to the frequency deviation. The duration of the stimulation pulse is adjustable independently of the amplitude. The output signal is applied between two electrodes which are implanted in the vicinity of the cells to be excited and can be multiplexed to excite several pairs of electrodes in succession by an electronic circuit advanced by signal segments at a frequency at one end of the deviation range.

8 Claims, 6 Drawing Figures

METHOD OF NERVE STIMULATION AND A STIMULATOR FOR THE APPLICATION OF THE METHOD

This invention relates to a method of excitation of living nerve or muscle cells for example and to a device for carrying out the method. The device is of simple constructional design and of sufficiently small size to permit insertion in the human body in the vicinity of the cells to be excited, the amplitude of the signal delivered being independent of the coupling between an excitation emitter which is located outside the body and a receiver which is implated "in situ."

The method according to the invention and the associated stimulator have the design function of delivering, by means of two electrodes suitably placed within the body, pulses which are intended to generate artifically the action potential of a group of nerve cells, for example. The stimulator according to the invention is "implanted," or in other words fixed either permanently or "semi-permanently" within the body at the time of a surgical operation. the stimulator is supplied with energy and controlled from the exterior by an transmitter which is capable of varying the duration, the recurrence time and the amplitude of the stimulation peaks in order to permit adaptation to the physiological constants of the different nerves.

It is known that a large number of electronic devices for the excitation of nerve cells which control different organs have been put on the market in recent years. Some of these devices are connected to an external control unit by means of two lead wires but this has a disadvantage in that a connection passes through the body tissues whereas it is preferable to dispense with such a connection in order to remove any danger of infection and to ensure comfort of the patient. Further intergrated devices are inserted in the patient's body but are subject to a disadvantage in that they entail the need for a surgical operation when one of the parameters of the device is to be changed or when the supply source is to be regenerated.

Stimulators of this type are employed in particular for the excitation of the cardiac muscle or for the excitation of the nerves. In the case of the cardiac regulator, electrical pulses are applied to the ventricles of the patient's heart so as to initiate the beats of the cardiac muscle.

Stimulators are required to conform to a large number of specifications. They have to be miniaturized, they have to be electrically insulated within the body whilst a connection with the exterior should preferably be established by mutual induction, and they must not be provided with power sources which are liable to suffer degradation in the course of time. The entire quantity of energy which is necessary for ensuring correct operation of these devices must be supplied by the external control unit. Moreover, these circuits must be highly reliable in order to avoid the need to perform surgical operations on the patient. It should also be made possible to vary the time-duration, the recurrence and the amplitude of the stimulation peaks in order to permit adaptation to the physiological constants of the different nerves. Modulation of the amplitude of the peaks makes it possible to vary the number of nerve fibers excited whereas modulation of the recurrence produces a variation of the stimulation frequency. These two phenomena have the combined effect of modifying the intensity of action applied to a nerve and are the two parameters which must be strictly controlled in any nerve stimulator. The current applied by the stimulator to the nerve tissue is preferably two-phase, or in other words has a zero mean value, in order to prevent any phenomenon of electrode polarization and electrolysis.

It is known that nerve stimulators of the type comprising an external transmitting coil and a receiving coil have already been constructed. These stimulators operate on the principle of amplitude modulation, the signal induced in the receiving coil being rectified and filtered, then directed into a pair of electrodes in order to excite the appropriate nerves. This amplitude modulation system suffers from one major drawback in that the coupling between the transmitting coil and the receiving coil is highly dependent on the distance between the transmitter and the receiver as well as the respective orientations of these latter.

One device which makes it possible to dispense with the need for coupling between the two coils is described in U.S. Pat. No. 3,773,051 of Nov. 20th, 1973. In this patent, the amplitude of the stimulation signal is independent, within a given range, of the amplitude of the signal produced by the receiver at the time of transmission since it is proportional not to the amplitude but to the width, that is to say to the time-duration of the transmitted signal. This system does not permit indpendent adjustment of the amplitude and the width of peaks; the width of the stimulation signal is fixed whilst the width of the transmitted signal determines its amplitude. Moreover, the maximum recurrence frequency is also limited by the width of the transmitted signals. Furthermore, the device is complex both in design and construction. It therefore contains a large number of components, thus calling for a special miniaturized circuit.

The precise object of the present invention is to provide a method of excitation of nerve and muscle cells and a stimulator for the practical application of the method in order to overcome the disadvantages of variable coupling between transmitting and receiving coils without relating the stimulation amplitude to the duration of the signal which drives the electrodes, the stimulator being simple to manufacture and of small overall size.

The method in accordance with the invention consists in emitting during a predetermined period t a signal having a frequency $f$, said frequency $f$ being adjustable about a frequency $f_0$; this frequency is adjusted by means of a circuit for converting voltage to frequency variation and passed into a transmitter; the signals transmitted by the transmitter are collected in a receiver (such as a receiving coil, for example) and the collected signal is processed so as to obtain an output signal having an amplitude which is proportional to the frequency difference $f - f_0$ and having a duration which is adjustable as a function of the transmission period t. Thus the amplitude variation of the signal which drives the stimulation electrodes is produced by varying the frequency of the signal transmitted by the transmitter within a frequency range $\Delta f$ about $f_0$. The electrode drive signal is thus almost completely independent of the amplitude of the signal received by the receiving coil on condition that this latter exceeds a predetermined threshold value.

The frequency modulation is of small magnitude or, in other words, the frequency band $\Delta f$ is considerably lower than the frequency $f_0$; this does not prevent the possibility of covering the entire range of amplitude of desired signals by adjusting the coefficient of proportionality between the variations of amplitude and the frequency difference $f - f_O$. In comparison with the device described in U.S. Pat. No. 3,773,051, the invention makes it possible to vary independently the width of the transmitted tube trains and the amplitude of the stimulation peaks. This in turn makes it possible, within the recurrence intervals of the stimulation peaks and in the case of any one nerve, to intercalate a maximum and constant number of peaks in the case of other nerves.

Furthermore, the practical application of the method in accordance with the invention has a low degree of complexity and limits the total number of elements of small size which are inserted in the body.

The device for carrying out the invention is entirely supplied by the signals generated in the receiving coil, thus ensuring energy independence of the device.

In accordance with one embodiment of the invention, there is transmitted an alternating-current signal made up of sections having a variable time-duration $t_1, t_2 o..t_i$ and having respective frequencies $f_1, f_2 ... f_i$. These signals are collected in the receiving coil and are processed in a frequency-voltage converter so as to produce output signals having an amplitude proportional to the frequency difference $f_{i-fo}$ and a duration proportional to $t_i$ to pairs of different electrodes in order to excite different nerves at a predetermined frequency.

The invention is also directed to a nerve stimulator which serves to carry out the method and delivers by means of electrodes pulses which are capable of controlling nerve cells, said stimulator being activated by a transmitter which delivers signals having a given frequency $f$ in the vicinity of a reference frequency $f_O$ for a predetermined period of stimulation $t$, comprising in series:
- a receiving coil tuned to the frequency $f_O$,
- a filter circuit at the output of the receiving coil, comprising means for delivering a rectangular signal having a duration t from the alternating-current signal obtained at the output of the coil,
- a stabilizing circuit placed after the filter circuit, comprising means for delivering a rectangular signal having a duration t and a constant amplitude from the signal delivered at the output of the filter circuit,
- a frequency-variation converter comprising means for delivering a signal having an amplitude which is proportional to $f-f_O$ during a time interval $t$,
- electrodes driven by the output signal of the frequency-variation converter and connected to the terminals of said converter.

In an alternative embodiment of the invention, a power stage is added between the frequency-voltage converter and the nerve-excitation electrodes.

In the embodiment of the invention which consists in transmitting a train formed of sections of signals having different frequencies, there is employed in the nerve stimulator a multiplexing assembly and a conventional control counter for transmitting a series of electrical signals in a predetermined sequence to pairs of electrodes connected in parallel at the output of the multiplexer.

Further properties and advantages of the invention will become more apparent from the following description of exemplified embodiments which are given by way of explanation without any limitation being implied, reference being made to the accompanying figures, where.

Figure 1:
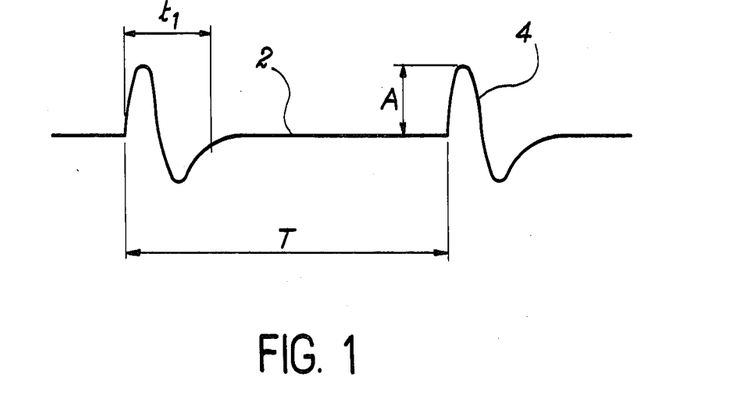
FIG. 1 shows the shape of a recurrent electrical pulse applied to the nerve excitation electrodes.

There is shown in FIG. 1 a nerve stimulation signal 2, each pulse such as the pulse 4 being formed by a positive half-wave and a negative half-wave, the time-width or duration of the pulse is $t_1$ and the amplitude is designated by the arrow A; the recurrence time, namely the time interval between the drive provided by two identical signals, is T.

Figure 2:
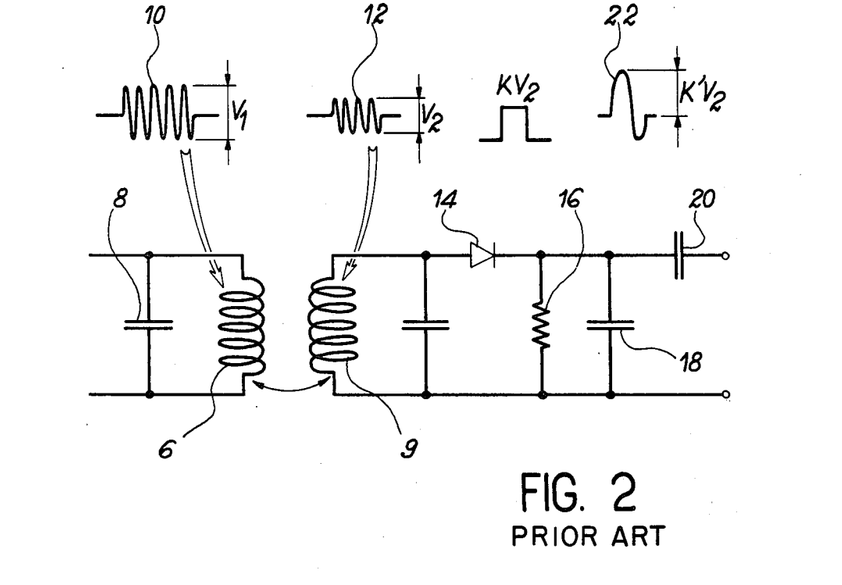
FIG. 2 is a diagram showing a nerve stimulator of the prior art.

There is shown in FIG. 2 a diagram of a stimulator of the prior art comprising an transmitter represented schematically by an inductance coil 6 and a capacitor 8 which are turned to the frequency $f_O$ and emit the signal 10 having a zero mean value and an amplitude $V_1$. An electrical signal 12 having an amplitude $V_2$ having the same frequency $f_O$ appears in the receiving coil 9 by inductive coupling. The diode 14 rectifies the signal which is filtered through the resistor 16 and the capacitor 18, to produce a pulse $KV_2$ then differentiated by the capacitor 20 so as to produce at the output the signal 22 having an amplitude $K'V_2$. As has already been stated, this very simple arrangement results in the face that the output signal is very closely dependent on the coupling between the emitting and receiving coils, thus setting geomtrical limitations in regard to the respective localization and orientation of said coils.

Figure 3:
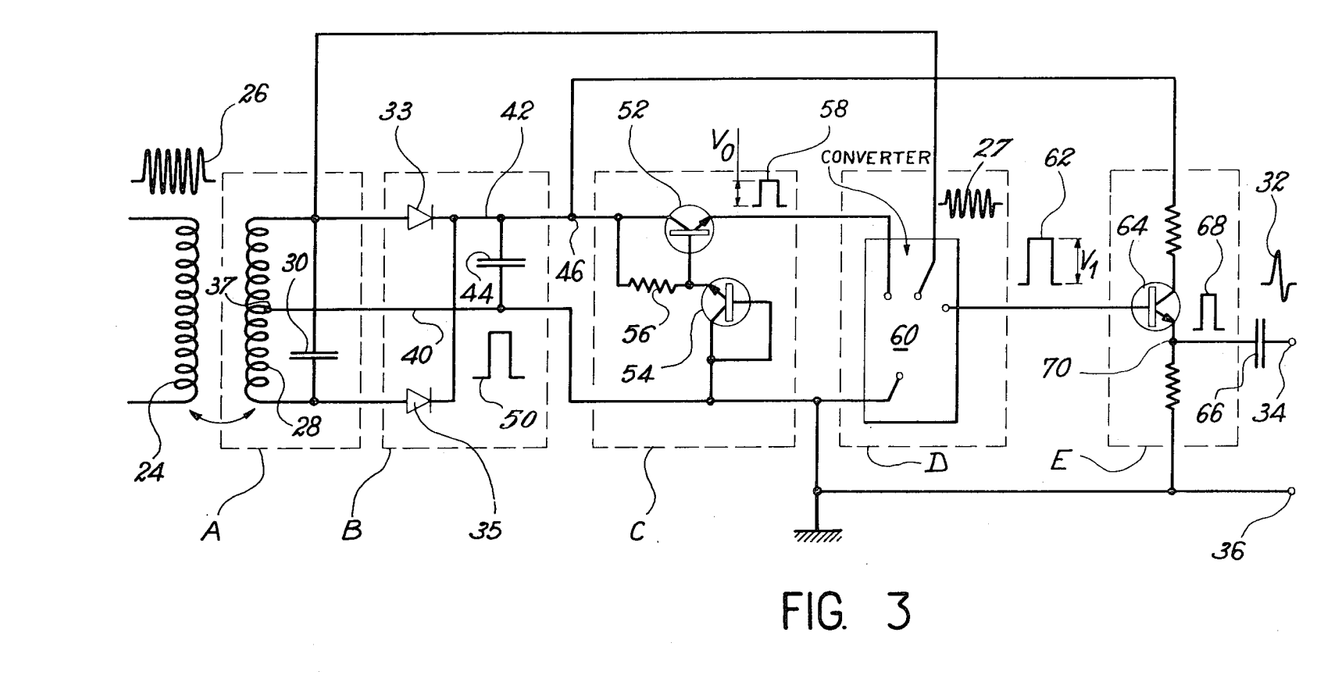
FIG. 3 shows a nerve stimulator in accordance with the invention.

In FIG. 3, there is shown the diagram of a stimulator in accordance with the invention comrprising a transmitting coil 24 which transmits the signal 26 at the frequency $f_1$. The receiving coil is formed by the inductor 28 having a value L and the capacitor 30 having a value C which are chosen so as to ensure that $f_O = 2\pi\sqrt{LC}$. After the receiving coil, there has been placed in series a rectifying and filtering circuit B, a voltage-regulating circuit C, a circuit D for converting frequency variation to voltage, a power circuit E for delivering a final signal 32 between the terminals 34 and 36 to which the electrodes are connected. The current-rectifying circuit comprises two diodes 33 and 35 connected between the ends of the winding of the inductor 28 and the lead 40 extends from the central tapping 37 of the receiving coil 28. A filter capacitor 44 is placed between the lead 40 and the lead 42, the signal appearing at the terminal 46 under the influence of the signal 27 induced by the signal 26 being as shown at 50. A voltage-regulating system of known type as shown by way of example in the figure comprises a transistor 52 and a transistor 54 connected as a Zener diode. A resistor 56 is placed between the base of the transistor 52 and the emitter. The stabilized rectangular voltage of magnitude $V_0$ is obtained on the emitter of the transistor 52 as shown at 58. Said voltage as well as the signal 27 induced in the receiving coil are applied to the converter 60. The signal 58 serves essentially to supply the converter and to establish the duration of the signal whilst the signal 27 serves to record the frequency f in order to calculate $f - f_0$. There is obtained at the output of the converter 60 the output voltage $V_1$ which is shown at 62 and is equal to $K (f_1 - f_0)$, the coefficient K being a multiplication factor which is characteristic of the converter 60. There is shown at E an impedance matching and shaping stage comprising a transistor 64 with an emitter follower output connection through a capacitor 66 which delivers the output signal 32 resulting from the conversion of the signal 68 which appears at the terminal 70. In one embodiment of the invention, the receiving coil 28 detects a ransmitted signal whose frequency varies between 310 and 340 $KH_z$. As mentioned earlier, the signal, which is detected in "full wave" by the coil 28 at its central tapping 37 and then filtered, supplies the frequency-variation converter during each transmission by means of the stabilization stage and the power output stage. The regulating stage C energizes the frequency-variation converter 60 at constant voltage during the transmission period.

The receiving coil having a central tapping is turned for example to the maximum frequency transmitted at 340 $KH_z$. The coil delivers on the one hand the frequency information to the converter 60 and on the other hand, after rectification and filtering, the supply voltage to the regulator C. The use of a converter of the "phase loop" type entails the need for a supply which is stabilized by a regulator. This regulator C is constituted by a transistor 52 and a second transistor connected as, and functioning as, Zener diode 54, which establishes a reference voltage between the base and ground. In a preferential embodiment of the invention, the converter 60 is, for example, a "phase loop" converter of type CD 4046 A manufactured by RCA. This converter has been chosen so as to carry out the demodulation by reason of its low consumption which is of the order of one milliampere and delivers a filtered signal whose amplitude is proportional to the frequency difference with respect to the frequency $f_0$.

We may write with a good approximation:

$V_1 = (V_O/2)$ and $\Delta f$ is the bandwidth of the
converter $(f - f_O)/(\Delta f)$, where $V_O$ is the supply voltage.

It is readily apparent that any other frequency-voltage converter is suitable for the practical application of the invention provided that its consumption remains within reasonable limits of the order of 1 mA.

The power stage responding to the output of the demodulator supplies the current to the electrodes which are fixed on the member to be excited. The variation of the output current at 220 ohms is between 0 and about ten milliamperes.

Figure 5:
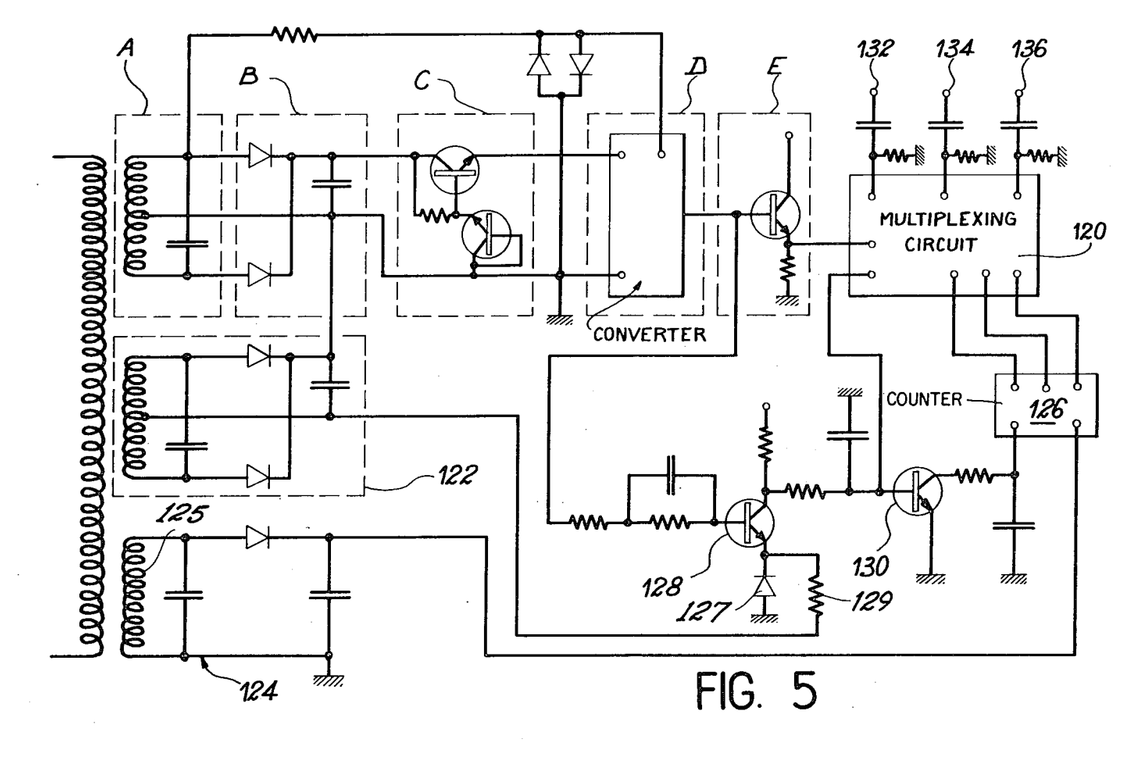
FIG. 5 shows a nerve stimulator in accordance with the invention which comprises a multiplexer for switching towards different pairs of electrodes in parallel.

FIG. 5 is a schematic diagram showing the general construction of the polynerve stimulator which comprises the same elements A, B, C, D, E as the diagram of FIG. 3. In addition, the stimulator comprises a multiplexing circuit 120 which supplies the outputs 132, 134, 136 sequentially, a negative supply 122, two threshold logic stages 128 and 130 and a receiving circuit 124 for the reset signal of the counter 126. The elements 130 and 124 are connected to the counter 126 which controls the multiplexing circuit 120 by suitable circuitry in order to deliver the reset and forward motion pulses thereto. By way of example of practical design, the multiplexing circuit 120 can be of the type known as CD 4051 A and the counter 126 can be of the type known as CD 4024, both of these devices being manufactured by RCA. The signals are delivered by the multiplexing circuit 120 to the electrodes which are connected between ground and a outputs 132, 134, 136.

Figure 4:
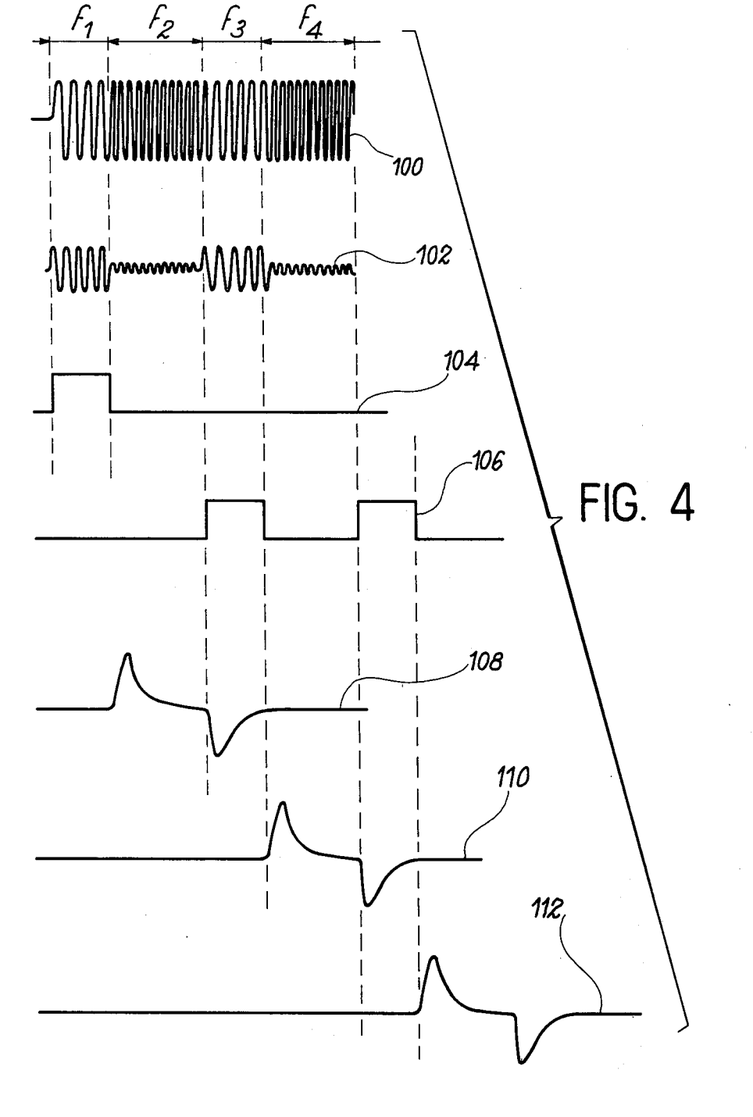
FIG. 4 shows time-dependent variations of the different signals from the time of transmission by the transmitter which induces signals in the receiving coil up to the electrode drive signals in the embodiment of the invention in which a number of nerves are excited.

There are shown in FIG. 4 the signals corresponding to the processing of a signal 100 which is transmitted continuously by the transmitter. This signal is made up of a number of sections, namely a first section at a frequency $f_1$ followed by signals at the frequencies $f_2, f_3$ and $f_4$. The signal produced in the receiving coil 28 has the shape indicated on the curve 102. The signal having the frequency $f_1$ which is the lowest frequency is detected by the tuned circuit as constituted by the receiving coil of the circuit 124 shown in FIG. 5. Said signal constitutes the counter reset signal shown on the curve 104. The following signal having a frequency $f_2$ and a duration equal to that of the stimulation signal produces at the output of the frequency-voltage converter a signal whose amplitude is dependent on the frequency differences $f_O - f_2$ and which is switched by the multiplexer 120 (FIG. 5) towards a channel of the multiplexer 120 to which are connected the electrodes corresponding to one particular nerve: the signal which follows next is transmitted at a frequency $f_3$ which is very close to $f_0$ so that the signal delivered by the converter becomes lower in value than the inhibition threshold of the multiplexer 120 and initiates the forward motion of the counter 126 by means of the circuit 130. The multiplexer is then positioned in a second channel to which are connected the electrodes corresponding to a second nerve. The following emission of the frequency $f_4$ delivers the stimulation signal to the electrodes which are implanted in the vicinity of this second nerve: the signals for initiating counter motion are represented on curve 106, the signal for excitation of the first nerve is represented on curve 108, the signal for excitation of the second nerve is represented on curve 110 and the signal for excitation of a third nerve is represented on curve 112.

As mentioned before, circuit 122 is a negative voltage supply. It is a combination of a tuned coil and a detector similar to those shown in circuits A and B, but instead of the negative terminal of the detector being grounded, in the case of circuit 122, the positive terminal is grounded and the negative output terminal is furnished to a current limiting resistor 129, so that the energization of the transistor 128 instead of being between a positive voltage and ground, as in the case of circuit E, is between a positive voltage and a negative voltage provided by the circuit 122. The diode 127 prevents the ungrounded side of that diode and its connection to the transistor 128 and the resistor 129 from being pulled appreciably above ground potential. Of course the positive voltage supply for the transistor 128 and for the circuit E may, as in the case of FIG. 3, be derived from the output of the detector B. The need for the negative voltage supply 122 is simply because it is desired to provide an output for the transistor 128 with a pulse from the output of circuit D which pulse is of a magnitude lower than that which will overcome the threshold at which base current will flow in the transistor of circuit E and produce an output from the circuit of E. An "inhibit" signal is provided directly to the multiplexing circuit 120 to prevent switching transients of that circuit from affecting the outputs 132, 134 and 136 and the inverter circuit 130 provides a signal of appropriate polarity for advancing the circuit 126.

The circuit 124 includes a receiving coil 125 tuned to a frequency outside of the range of frequencies used for nerve stimulation followed by a halfwave detector which produces, in response to such a frequency, a reset pulse provided to the reset terminal of the counter 126.

Figure 6:
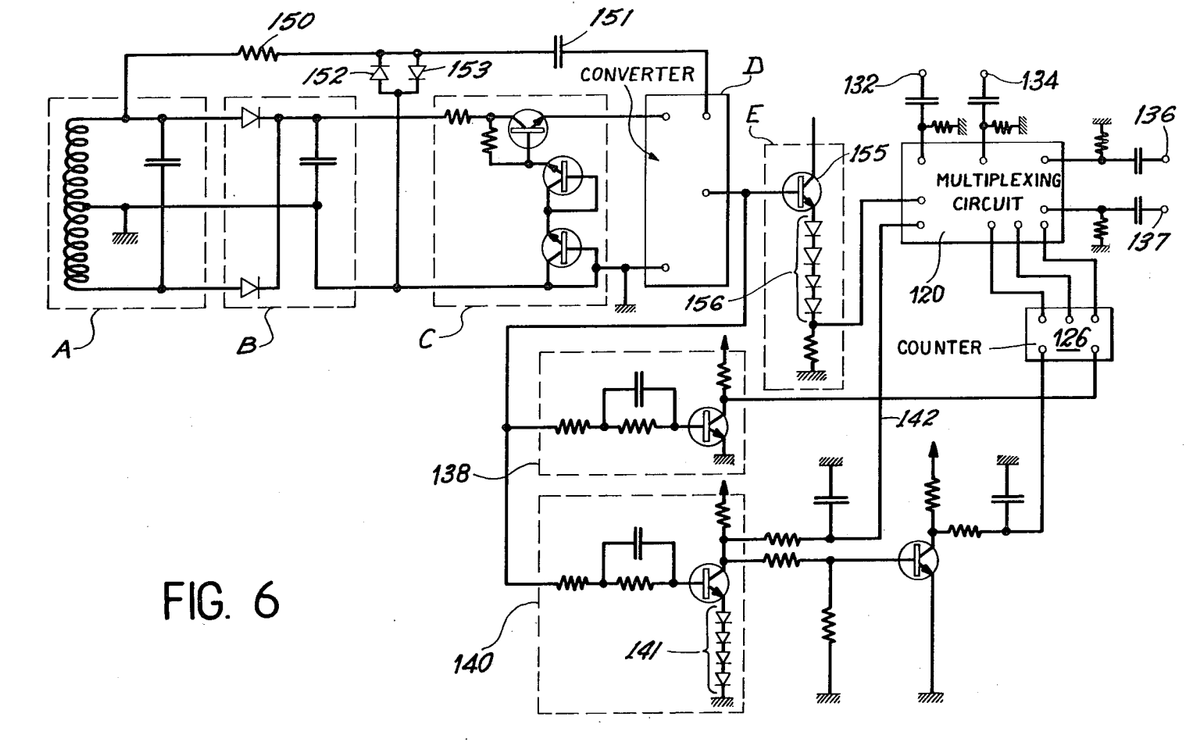
FIG. 6 shows another form of multiplex nerve stimulator according to the invention.

There is shown in FIG. 6 an alternative form of construction of the polynerve stimulator which also comprises the elements A, B, C, D and E, a multiplexing circuit 120 which supplies the outputs 132, 134, 136 and 137 sequentially and a counter 126. The circuits 122 and 124 of FIG. 5 have no counterpart in this example of construction. Control of zero-reset and forward motion of the counter 126 is performed by means of threshold circuits 138 and 140 respectively, to which is applied the output of the frequency-variation converter D. The circuit E is modified so that this latter also becomes a threshold circuit.

When the output voltage of D exceeds this threshold value, power control is ensured on the particular output which is selected by the multiplexer 120.

When this voltage falls below the threshold value which is established by the circuit 140, this accordingly results in inhibition of the multiplexing circuit 120 and forward motion of the counter 126. When said voltage rises above the threshold value established by the circuit 138, this circuit accordingly produces a signal for resetting the counter 126.

More particularly, the connection between circuit A and circuit B serves to transmit to the circuit B the frequency signal picked up in circuit A, circuit D serving to provide again at its output a signal of which the amplitude is a function of that frequency and to provide that output to circuit E, and in this case also to circuits 138 and 140. The resistance 150 serves to limit the current and the capacitor 151 serves to block the direct current and to pass only the alternating component. The diodes 152 and 153 limit the amplitude of the alternating signal.

the circuit E generates the excitation signal supplied to the nerves through the multiplexing circuit 120, functioning in this regard as a power stage and also as a circuit setting a threshold above which the signal processed by the circuit D is applied to the nerves and below which no output signal is produced. The power stage function is provided by the transistor 155 and the threshold is provided by the diode chain 156.

The outputs 132, 134, 136 and 137 represent outputs connected to different nerves and, of course, still more such outputs could be provided.

The circuit 140 corresponds to the circuits 122, 128, 130 of FIG. 5 and serves to advance the counter 126. The circuit 138 is the circuit which controls the resetting of the counter 126, and therefore corresponds to the circuit 124 of FIG. 5. The circuits 140 and 138 are threshold circuits having respectively different thresholds for response to the output voltage of the circuit D, which is to say that they respond to two different values of the frequency of the signal picked up in A, a counter-advancing frequency in the case of circuit 140 and a counter-resetting frequency in the case of circuit 138. The diode chain 141 defines the difference in these two thresholds. The threshold of the circuit 140 is below that set by the diode chain 156 in the circuit E. Between the circuit 140 and the counter 126 is a coupling stage which "inverts" the polarity or logic of the circuit 140 output to meet the requirements of the reset input of the particular counter unit 126. The output signal of the circuit 140, however, is of the polarity appropriate for acting directly on the multiplexing circuit 120 over the connection 142 to inhibit the multiplexing circuit during the advance of the counter 126, in order to prevent the stimulation signal generated by the circuit E from being falsely sent to an electrode during the switching transition.

We claim:

1. A method for electric excitation of living cells by means of an electromagnetically inductive receiver implanted in a living body and equipped with output electrodes, comprising the steps of:
   producing an alternating electromagnetic induction field at the location of said receiver of a frequency variable about a reference frequency $f_0$ by means of a transmitter external to said body operated at a frequency $f$ so set and for a period so selected that the requency difference $f - f_0$ corresponds to a desired amplitude of a cell excitation pulse and the selected period corresponds to a desired cell excitation pulse duration, and repeating said field producing step at predetermined intervals to the extent further cell excitation is desired;
   detecting said induction field in said receiver to collect energy therefrom for operating said receiver, and
   detecting in said receiver the extent of said frequency difference $f - f_0$ of said induction field and producing in response thereto at said output electrodes a cell excitation signal of an amplitude corresponding to said frequency difference $f - f_0$ and of a duration determined by said selected period.

2. A method as defined in claim 1 in which between some successive performances of said field producing step the following additional steps are performed:
   producing for a period of time an alternating electromagnetic induction field at a frequency outside of the frequency range utilized for producing a cell excitation signal,
   detecting such period of said production of a field of a frequency outside said cell excitation frequency range, and
   switching the output of said receiver, in response to the performance of the last-mentioned detecting step, to a different pair of cell excitation electrodes among a set of a plurality of pairs of cell excitation electrodes implanted in said living body, said switching step being performed progressively among said pairs of electrodes in response to successive performances of said detecting step respectively in successive performances of the method.

3. A method for electric excitation of living cells by means of an electromagnetically inductive receiver implanted in a living body and equipped with output electrodes, comprising the steps of:
   producing an alternating electromagnetic induction field at the location of said receiver by means of a variable frequency transmitter external to said body successively at frequencies $f_1, f_2, f_i$ 2 $f_i$ respectively for durations $t_1 t_2 \ldots t_i$;
   detecting said induction field in said receiver to collect energy therefrom for operating said receiver, and
   detecting in said receiver the several frequencies $f_1$, $f_2 \ldots f_i$ and in response to at least one of them switching the output of said receiver from one to another pair of cell excitation electrodes among a set of a plurality of pair of cell excitation electrodes implanted in said living body, and in response to others of said frequencies $f_1, f_2 \ldots f_i$ producing at one pair of said electrodes a cell excitation signal of an amplitude and polarity determined by the difference between the particular frequency and a reference frequency $f_0$ and of a duration determined by the corresponding of the period durations $t_1, t_2 \ldots t_i$.

4. A stimulator for implantation in a living body and there delivering, by means of electrodes, pulses which are capable of electrically exciting living cells in response to a frequency modulated electromagnetic transmitter external to said living body, said stimulator comprising, in combination:

a receiving coil tuned to a predetermined reference frequency $f_0$;

first detecting means responsive to the output of the receiving coil for delivering a continuous d.c. signal having a duration equal to the duration of an alternating current signal obtained at the output of the receiving coil;

stabilizing circuit means responsive to said first detecting means for providing a continuous d.c. output signal having a constant as well as a duration equal to the duration of said alternating current signal;

frequency detection means, having a first input connected for response to the output of said receiving coil and having a second input connected to the output of said stabilizing circuit, for delivering an output signal having a magnitude which is proportional to the difference between the detected frequency $f$ and said reference frequency $f_0$ during a time interval $t$ equal to the duration of said alternating current signal obtained at the output of the receiving coil and for delivering no significant output at other times;

pulse shaping circuit means for producing a cell stimulating pulse in response to the output of said frequency detection means, having a control input connected to the output of said frequency detection means, said pulse having an amplitude which is proportional to said frequency difference $f-f_0$ and a duration determined by said time interval $t$, and output means, including electrodes implanted in said living body, responsive to the output of said pulse shaping circuit means for providing cell stimulating pulses to living cells adjacent to said electrodes.

5. A stimulator as defined in claim 4, in which said output means comprises a power stage for driving said electrodes in response to the output of said pulse shaping means.

6. A stimulator as defined in claim 4, which further comprises:

switch control pulse producing means responsive to the output of said frequency detection means;

a second receiving coil tuned to a frequency outside the range of frequencies utilized for producing cell stimulation pulses;

second detecting means responsive to the output of said second receiving coil for detecting said second frequency outside a range of frequencies utilized for producing cell stimulation pulses;

a control counter connected to the output of said switch control pulse producing means so as to be advanced thereby in response to said output and connected to the output of said second detecting means so as to be reset thereby, and switching means responsive to said control counter for sequentially switching, to connection with the output of said pulse shaping means, different electrode pairs of said electrodes for sequential stimulation of different cells in response to successive portions of the output of said pulse shaping means.

7. A stimulator as defined in claim 4, including means for deriving power from the output of said first detecting means and thereby supplying all the electric power needed for the operation of the receiver, said power deriving means including a connection between said output of said first detecting means and said pulse shaping circuit for energization of the latter.

8. A stimulator as defined in claim 6, in which said switch control producing means is constituted to provide an output for advancing said counter in response to an output of said frequency detection means corresponding to a frequency which is closer in value to said reference frequency than frequencies utilized for producing cell stimulation pulses.

* * * * *

UNITED STATES PATENT OFFICE
CERTIFICATE OF CORRECTION

PATENT NO. : 4,057,069
DATED : November 8, 1977
INVENTOR(S) : Auguste DORFFER ET AL.

It is certified that error appears in the above-identified patent and that said Letters Patent are hereby corrected as shown below:

In claim 3, line 58, after "frequencies" "$f_1, f_2 f_{i2} f_i$" should be corrected to read -- $f_1, f_2 ... f_i$ --.

In claim 6, line 13, before "frequency", the word "second" should be inserted.

Signed and Sealed this

Fourth Day of April 1978

[SEAL]

Attest:

RUTH C. MASON
Attesting Officer

LUTRELLE F. PARKER
Acting Commissioner of Patents and Trademarks